United States Patent
Servidio et al.

(10) Patent No.: US 11,123,085 B2
(45) Date of Patent: Sep. 21, 2021

(54) CUTTING TOOL POSITIONED BY FLEXIBLE ROD FOR REVISION SURGERY

(71) Applicant: Howmedica Osteonics Corp., Mahwah, NJ (US)

(72) Inventors: Damon J. Servidio, Towaco, NJ (US); Scott G. Logan, Oak Ridge, NJ (US); Bryan D. Springer, Charlotte, NC (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 16/380,590

(22) Filed: Apr. 10, 2019

(65) Prior Publication Data

US 2019/0314041 A1 Oct. 17, 2019

Related U.S. Application Data

(60) Provisional application No. 62/656,102, filed on Apr. 11, 2018.

(51) Int. Cl.
*A61B 17/16* (2006.01)
*A61B 17/17* (2006.01)

(52) U.S. Cl.
CPC ........ *A61B 17/1675* (2013.01); *A61B 17/164* (2013.01); *A61B 17/1617* (2013.01); *A61B 17/1631* (2013.01); *A61B 17/1764* (2013.01)

(58) Field of Classification Search
CPC ............ A61B 17/1617; A61B 17/1631; A61B 17/1633; A61B 17/164; A61B 17/1675; A61B 17/1714; A61B 17/1764
See application file for complete search history.

(56) References Cited

U.S. PATENT DOCUMENTS

| | | | |
|---|---|---|---|
| 4,062,412 A | 12/1977 | McIlvanie | |
| 4,135,507 A | 1/1979 | Harris | |
| 4,141,225 A | 2/1979 | Varner | |
| 4,446,857 A | 5/1984 | Otte et al. | |
| 4,751,922 A * | 6/1988 | DiPietropolo | B23Q 5/043 606/80 |
| 4,791,919 A | 12/1988 | Elloy et al. | |
| 4,808,186 A | 2/1989 | Smith | |
| 4,825,857 A | 5/1989 | Kenna | |
| 4,851,008 A | 7/1989 | Johnson | |

(Continued)

FOREIGN PATENT DOCUMENTS

| EP | 0 355 411 A1 | 2/1990 |
|---|---|---|
| FR | 2288506 A1 | 5/1976 |

(Continued)

OTHER PUBLICATIONS

European Communication for Application No. EP08754440.9 dated Jan. 21, 2015.

(Continued)

*Primary Examiner* — Matthew J Lawson
*Assistant Examiner* — Lisa Nguyen
(74) *Attorney, Agent, or Firm* — Lerner, David, Littenberg, Krumholz & Mentlik, LLP

(57) ABSTRACT

A revision is performed on a bone. A first cutting tool is placed over a rod inserted into the bone such that the rod extends through a cannula of the first cutting tool. The inserted rod is curved within the bone. A hole is formed in the bone with the first cutting tool placed over the curved rod.

21 Claims, 8 Drawing Sheets

(56) References Cited

U.S. PATENT DOCUMENTS

| | | |
|---|---|---|
| 4,907,578 A | 3/1990 | Petersen |
| 4,921,501 A | 5/1990 | Giacometti et al. |
| 5,041,114 A | 8/1991 | Chapman et al. |
| 5,053,035 A | 10/1991 | McLaren |
| 5,053,037 A | 10/1991 | Lackey |
| 5,122,134 A | 6/1992 | Borzone et al. |
| 5,135,527 A | 8/1992 | Ender |
| 5,234,433 A | 8/1993 | Bert et al. |
| 5,336,265 A | 8/1994 | Serbousek et al. |
| 5,374,235 A | 12/1994 | Ahrens |
| 5,387,216 A | 2/1995 | Thornhill et al. |
| 5,514,140 A | 5/1996 | Lackey |
| 5,562,674 A | 10/1996 | Stalcup et al. |
| 5,618,286 A | 4/1997 | Brinker |
| 5,674,223 A | 10/1997 | Cipolletti |
| 5,741,264 A | 4/1998 | Cipolletti |
| 5,776,204 A | 7/1998 | Noble et al. |
| 5,826,776 A | 10/1998 | Schulze et al. |
| 5,830,216 A | 11/1998 | Insall et al. |
| 5,879,352 A | 3/1999 | Filoso et al. |
| 5,908,423 A | 6/1999 | Kashuba et al. |
| 5,957,925 A | 9/1999 | Cook et al. |
| 6,168,595 B1 | 1/2001 | Durham et al. |
| 6,193,723 B1 | 2/2001 | Cripe et al. |
| 6,205,411 B1 | 3/2001 | DiGioia, III et al. |
| 6,322,591 B1 | 11/2001 | Ahrens |
| 6,337,142 B2 | 1/2002 | Harder et al. |
| 6,416,517 B2 | 7/2002 | Harder et al. |
| 6,454,810 B1 | 9/2002 | Lob |
| 6,547,791 B1 | 4/2003 | Buhren et al. |
| 6,740,092 B2 | 5/2004 | Lombardo et al. |
| 6,875,237 B2 | 4/2005 | Dye |
| 6,949,101 B2 | 9/2005 | McCleary et al. |
| 7,008,425 B2 | 3/2006 | Phillips |
| 7,112,015 B2 | 9/2006 | Roberts et al. |
| 7,237,556 B2 | 7/2007 | Smothers et al. |
| 7,736,367 B2 | 6/2010 | Kuczynski |
| 7,993,348 B2 | 8/2011 | Conte et al. |
| 8,016,833 B2 | 9/2011 | Roger et al. |
| 8,117,950 B2 | 2/2012 | Kozak et al. |
| 8,187,280 B2 | 5/2012 | May et al. |
| 8,562,616 B2 | 10/2013 | May et al. |
| 8,789,447 B2 | 7/2014 | Kozak |
| 9,011,444 B2 | 4/2015 | Primiano et al. |
| 9,080,611 B2 | 7/2015 | Sander |
| 9,138,238 B2 | 9/2015 | Sordelet et al. |
| 9,149,282 B2 | 10/2015 | Servidio et al. |
| 9,232,950 B2 | 1/2016 | Chaney et al. |
| 9,282,981 B2 | 3/2016 | Chaney et al. |
| 9,480,482 B2 | 11/2016 | Sordelet et al. |
| 9,522,008 B2 | 12/2016 | Ferko et al. |
| 9,526,513 B2 | 12/2016 | Collazo et al. |
| 9,526,541 B2 | 12/2016 | Logan et al. |
| 9,623,487 B2 | 4/2017 | Kozak |
| 9,636,122 B2 | 5/2017 | Chaney et al. |
| 9,668,758 B2 | 6/2017 | Collazo et al. |
| 9,763,793 B2 | 9/2017 | May et al. |
| 10,149,763 B2 | 12/2018 | Krebs et al. |
| 2002/0107522 A1 | 8/2002 | Picard et al. |
| 2003/0069581 A1 | 4/2003 | Stinson et al. |
| 2004/0106923 A1 | 6/2004 | Swanson |
| 2004/0267267 A1 | 12/2004 | Daniels et al. |
| 2005/0055028 A1 | 3/2005 | Haines |
| 2005/0216007 A1 | 9/2005 | Woll et al. |
| 2005/0273102 A1 | 12/2005 | Powell |
| 2006/0264950 A1 | 11/2006 | Nelson et al. |
| 2006/0264952 A1 | 11/2006 | Nelson et al. |
| 2007/0123878 A1 | 5/2007 | Shaver et al. |
| 2013/0197517 A1 * | 8/2013 | Gross .................. A61F 2/4684 606/62 |
| 2013/0325007 A1 | 12/2013 | Beyar et al. |
| 2016/0199071 A1 | 7/2016 | Collazo |
| 2016/0199187 A1 | 7/2016 | Krebs et al. |
| 2017/0215855 A1 | 8/2017 | Nunan |

FOREIGN PATENT DOCUMENTS

| | | | |
|---|---|---|---|
| GB | 2232355 A | 12/1990 | |
| WO | WO-9427507 A1 * | 12/1994 | .......... A61B 17/175 |
| WO | 2005094705 A2 | 10/2005 | |
| WO | 2005096976 A1 | 10/2005 | |
| WO | 2006124764 A1 | 11/2006 | |

OTHER PUBLICATIONS

Extended European Search Report for Application No. EP08754440 dated Apr. 19, 2013.

International Search Report for Application No. PCT/US2008/06143 dated Sep. 29, 2008.

Karzenis, et al., 'Access to the medullary canal in closed antegrade femoral nailing: a technical report.' Archives of Orthopaedic and Trauma, Apr. 2003, p. 1; abstract; para [Introduction and "Technique"].

Stryker Corporation, Triathlon Revision Knee System: Surgical Protocol, pp. 1-92, 2016.

Stryker Corporation, Triathlon TS Knee System: Surgical Protocol, pp. 1-68, 2012.

* cited by examiner

CUTTING TOOL POSITIONED BY FLEXIBLE ROD FOR REVISION SURGERY

CROSS-REFERENCE TO RELATED APPLICATION

The present application claims the benefit of the filing date of U.S. Provisional Patent Application No. 62/656,102 filed Apr. 11, 2018, the disclosure of which is hereby incorporated herein by reference.

FIELD OF THE INVENTION

The present application relates generally to bone implant instrumentation, and in particular to systems for preparing bone to receive an implant.

BACKGROUND OF THE INVENTION

Joint replacement surgery or arthroplasty is an often performed surgical procedure to restore natural, pain-free operation of the knee. During a total knee arthroplasty (TKA), the diseased cartilage surfaces of the thighbone (femur), the shinbone (tibia) and the kneecap (patella) are replaced by prosthetic implants, and during subsequent revision surgeries of such TKAs, the original femoral, tibial, and patellar implants that have worn out are replaced with new implants. Both of these surgical procedures require alignment of the femoral and tibial components to a vertical or mechanical axis of the limb.

When the femoral and tibia bones are fully extended (i.e., the knee joint is in extension), a proximal-distal axis drawn through the center of a femoral head (proximal femur) passes through the knee joint in a healthy knee and along the tibial canal to the ankle joint. This proximal-distal axis is called the mechanical axis, and it is along this axis that a load is transmitted. However, the axis of the medullary canal of the femur may lie at an angle of up to 7 degrees from this mechanical axis along the coronal plane. The femoral canal also has an anterior bow along a plane parallel to the sagittal plane. As part of a surgical procedure to replace the distal portion of the femur, an intramedullary (IM) rod is typically inserted into the medullary canal to serve as a surgical guide. A cutting block is then mounted onto the IM rod and placed against the distal portion of the femur. The cutting block provides cutting guide surfaces for making the required cuts on the distal femur, such as distal, posterior, anterior, posterior chamfer and anterior chamfer cuts. It is important that the rod provide an accurate reference for the cutting block.

During revision surgeries, a hole is bored through the medullary canal of the distal femur. To prepare the hole, a rigid and straight IM rod often is inserted into the medullary canal with the straightness of the rod maintained during insertion, as shown in FIG. 1. The rod extends from the distal portion of the femur at an anterior position, due to its straightness, in order to extend as closely as possible along the axis of the medullary canal. A reamer of uniform diameter is then mounted on the IM rod and driven into the medullary canal to enlarge the canal for receipt of a stem of a trial implant and subsequent replacement femoral implant. A distal portion of the reamed hole is generally biased towards an anterior side of the bone due to the placement of the IM rod, and a combination of the bow in the medullary canal and the straightness of the IM rod causes the reamer to deflect and thus to move generally anteriorly within the medullary canal as the reamer moves proximally within the bone. Furthermore, upon subsequent reaming in preparation for a revision cone to be implanted into the distal portion of the femur, a cone reamer further enlarges the distal portion of the reamed hole while again being generally biased towards the anterior side of the bone. These procedures can result in undesired bone stock removal anteriorly, as well as improper positioning and sizing of the revision cone and the replacement femoral implant.

Accordingly, there is a need to improve the process for preparing the femur to receive a femoral implant during revision surgeries.

BRIEF SUMMARY OF THE INVENTION

In accordance with an aspect, a revision of a prior treatment of a bone may be performed on the bone, which may be a long bone. A substantially straight IM rod may be inserted at least partially into the medullary canal of the bone such that the IM rod is bent, which may be in an anterior direction, along an arc within the medullary canal. A first cutting tool is mounted onto the bent IM rod. The first cutting tool may be tapered and may be a drill or reamer having helical flutes. The first cutting tool mounted on the IM rod is then driven into the bone to form a hole in the bone. The first cutting tool, when mounted on the IM rod, may be driven along an axis at a transverse angle to a planar surface of the bone prepared during the prior treatment of the bone. A portion, which may be a stem, of a cutting jig may be inserted into the formed hole. The cutting jig may be inserted over the IM rod while the rod is still inserted into the bone or the IM rod may be removed prior to insertion of the cutting jig. When the cutting jig is properly inserted and aligned relative to the bone, a second cutting tool may be guided by cutting surfaces of the cutting jig to make one or more planar cuts on the bone configured to mate with corresponding surfaces of a permanent implant, such as a femoral component of a knee replacement system. With the IM rod reinserted into the bone or still in place such that the rod is bent along the arc within the medullary canal, a third cutting tool may be mounted onto the bent rod. The third cutting tool may be tapered and may be a straight fluted reamer. The third cutting tool, when mounted on the IM rod, may be driven along the axis at the transverse angle to the planar surface of the bone prepared during the prior treatment of the bone. In this manner, a bore may be formed for receipt of an implant such as a femoral cone.

In accordance with another aspect, a revision may be performed on a bone by a process. In a step of the process, a first cutting tool may be placed over a rod inserted into the bone such that the rod may extend through a cannula of the first cutting tool. The inserted rod may define a longitudinal axis and may be curved within the bone. In another step of the process, a hole may be formed in the bone with the first cutting tool while the first cutting tool is placed over the curved rod.

In some arrangements, a jig may be inserted into the formed hole and against an end of the bone. In some such arrangements, the inserted rod may be removed from the bone prior to the jig being inserted into the formed hole.

In some arrangements, a second cutting tool may be inserted between a set of spaced apart cutting guide surfaces of the jig to guide the second cutting tool in cutting the bone. In some such arrangements, the set of cutting guide surfaces may guide the second cutting tool in cutting a new planar surface of the bone defining a plane set an angle to a plane defined by an initial planar surface of the bone existing prior to the second cutting tool being inserted between the set of spaced apart cutting guide surfaces. In some such arrangements, the initial planar surface may be a distal surface, an anterior surface, or a posterior surface of the bone.

In some arrangements, the jig may include a base and a peg that may extend from the base. In such arrangements, the base may be abutted against an exterior surface of the bone and the peg may be inserted into the formed hole when the jig is inserted into the formed hole.

In some arrangements, the exterior surface of the bone may be a distal surface of the bone. In such arrangements, the base may be abutted against the distal surface to limit the depth the peg is inserted into the formed hole when the jig is inserted into the formed hole.

In some arrangements, the jig may be a cutting jig for use in the resection of condyles of the bone.

In some arrangements, the first cutting tool may be a drill or a reamer. When the first cutting tool is a drill, the hole formed in the bone is formed by drilling the hole in the bone. When the first cutting tool is a reamer, the hole formed in the bone is formed by reaming the hole in the bone.

In some arrangements, the first cutting tool may be tapered along a length of the first cutting tool. In some such arrangements, the first cutting tool may be a drill or reamer.

In some arrangements, an additional cutting tool may be placed over the rod such that the rod extends through a cannula of the additional cutting tool. In such arrangements, the hole may be drilled or reamed with the additional cutting tool to modify the hole.

In some arrangements, the first cutting tool may be slid off the rod to separate the first cutting tool from the rod prior to the placement of the additional cutting tool over the rod.

In some arrangements, the first cutting tool may include a helical cutting blade. In some arrangements, the additional cutting tool may have a generally frustoconical shape and may include a plurality of straight blades tapered generally towards a longitudinal axis of the additional cutting tool.

In some arrangements, the first cutting tool may be slid substantially along an arc defined by the rod that is curved within the bone during the placement of the first cutting tool.

In some arrangements, the bone may be a long bone. In such arrangements, the rod may be inserted into the long bone substantially along an arc to bend the rod. In some such arrangements, the rod may be substantially straight prior to the insertion of the rod into the bone.

In some arrangements, at least a portion of a shaft may be inserted into the formed hole after removing from the rod from the bone. A jig may be inserted against an end of the bone such that a base of the jig abuts an exterior surface of the bone. A second cutting tool may be inserted between a set of spaced apart cutting guide surfaces of the jig to guide the second cutting tool in cutting the bone.

In accordance with another aspect, a revision may be performed on a long bone by a process. In a step of the process, a substantially straight rod may be inserted into the long bone such that the rod bends. In another step of the process, a first cutting tool may be slid over the rod inserted into the long bone such that the rod may extend through a cannula of the first cutting tool. The first cutting tool may be a tapered drill or a tapered reamer and may include a helical cutting flute. In another step of the process, a tapered hole may be formed in the bone with the first cutting tool. In another step of the process, a jig may be placed against an end or side of the bone. In this manner, a base of the jig may be abutted against an exterior surface of the bone. In another step of the process, a second cutting tool may be inserted between a set of spaced apart cutting guide surfaces of the jig to guide the second cutting tool in cutting the bone. The set of spaced apart cutting guide surfaces may guide the second cutting tool in cutting a new planar surface of the bone to define a plane set an angle to a plane defined by an initial planar surface of the bone existing prior to the insertion of the second cutting tool between the cutting surfaces of the jig. The initial planar surface may be a distal surface, an anterior surface, or a posterior surface of the bone.

In some arrangements, the first cutting tool may be slid off the rod to separate the first cutting tool from the rod. An additional cutting tool then may be placed over the rod such that the rod extends through a cannula of the additional cutting tool. The additional cutting tool may be a reamer that may have a generally frustoconical shape and may include a plurality of straight flutes tapered generally towards a longitudinal axis of the additional cutting tool. The tapered hole may be reamed with the additional cutting tool to modify the tapered hole.

In some arrangements, the jig may be inserted into the tapered hole such that a peg extending from the base is received in the tapered hole.

BRIEF DESCRIPTION OF THE DRAWINGS

A more complete appreciation of the subject matter of the present invention and various advantages thereof may be realized by reference to the following detailed description and the accompanying drawings, in which.

DETAILED DESCRIPTION

Figure 1:
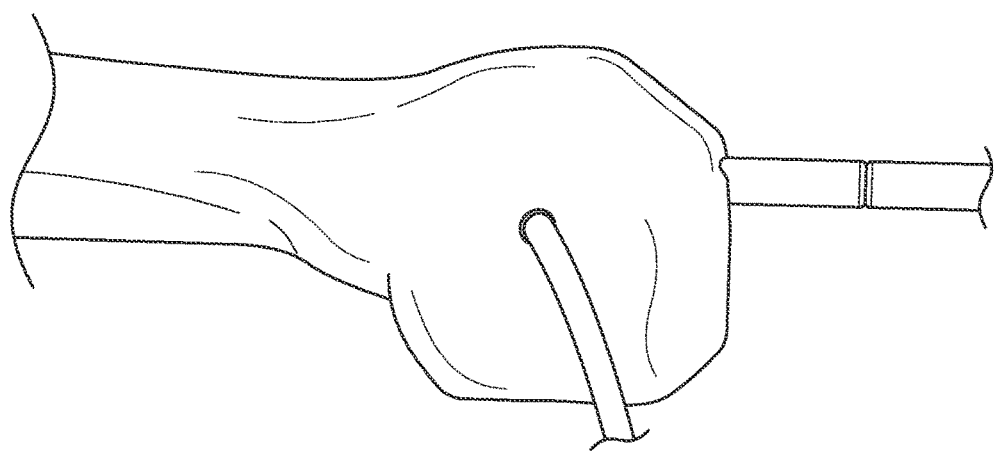
FIG. 1 is an elevation view of an IM rod inserted into a femur as known in the art.

As used herein, the term "distal" and variations thereof mean more distant from the heart, and the term "proximal" and variations thereof mean closest to the heart. The term "anterior" and variations thereof mean towards the front part of the body or the face, and the term "posterior" and variations thereof mean towards the back of the body. The term "medial" and variations thereof mean towards the midline of the body, and the term "lateral" and variations thereof mean away from the midline of the body.

Referring now to the drawings, as shown in FIGS. 2A-6, an instrumentation system for preparing a bone, in particular a long bone such as a femur, to receive an implant, in particular a revision implant, includes intramedullary (IM) rod 110, first reamer 120, jig 140, and second reamer 160. Each of first reamer 120, jig 140, and second reamer 160 are configured to be mounted on and to slide along IM rod 110.

Figure 2A:
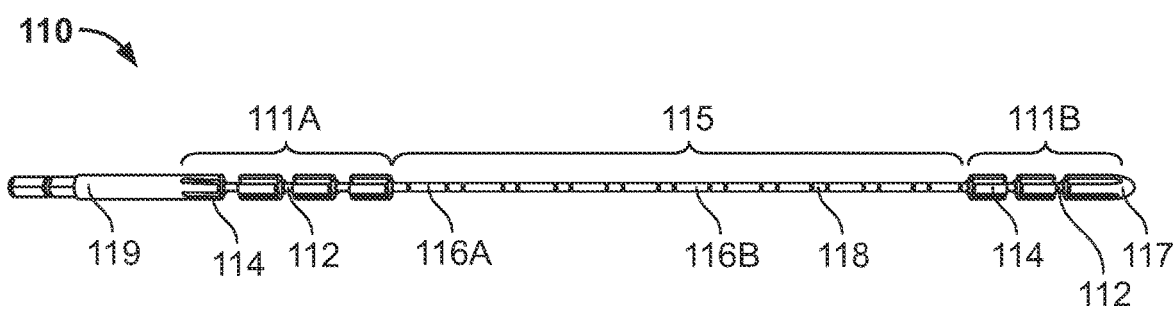
FIG. 2A is an elevation view of a flexible IM rod as known in the art.
Figure 2B:
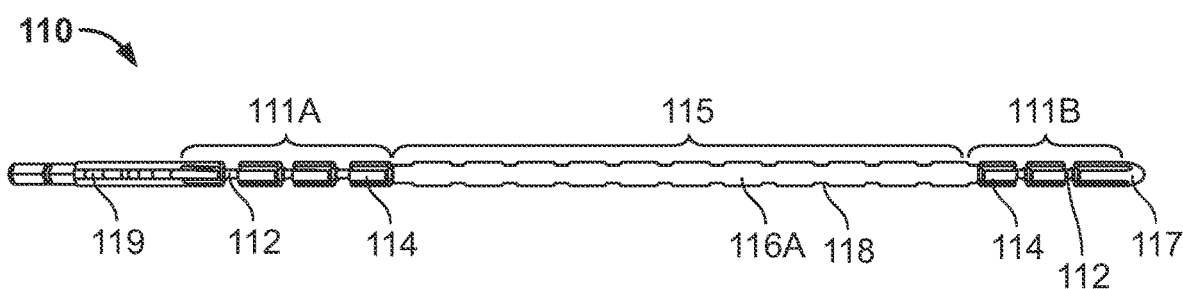
FIG. 2B is a plan view of the flexible IM rod shown in FIG. 2A.

IM rod 110, which in the example shown in FIGS. 2A and 2B is currently sold commercially as the Triathlon® Knee System FLEX IM Rod by Stryker Corp., includes cylindrical-like sections 111A, 111B on opposite sides of central section 115 as well as insertion section 117 and attachment section 119 each adjacent to one of the cylindrical-like sections and defining opposing ends of the rod. As best shown in FIGS. 2A and 2B, central section 115 includes opposing flat surfaces 116A, 116B providing the central section with a low profile. In this manner, central section 115 is generally flexible by human users in directions perpendicular to planes defined by each of flat surfaces 116A, 116B.

Each of cylindrical-like sections 111A, 111B include first cutouts 112 and second cutouts 114 intersecting the first cutouts 112 in a manner described with respect to the cutouts described in U.S. Pat. No. 9,526,541 ("the '541 patent"), which is hereby incorporated by reference in its entirety herein. In particular, each first cutout 112 has a directly opposing first cutout in which each of these cutouts extend in a direction generally parallel to a longitudinal axis defined by IM rod 110 along an inner portion of these cutouts nearest to the longitudinal axis of the rod and in respective directions away from the planes defined by flat surfaces 116A, 116B along outer portions on opposite ends of the inner portion of these cutouts. Four of second cutouts 114 are equally spaced apart around a diameter of the rod in each of cylindrical-like sections 111A, 111B such that the second cutouts define edges of first cutouts 112. In this manner, second cutouts 114 provide channels to ease the insertion of IM rod 110 into a patient's bone and to allow IM rod 110 to flex such that less force is needed to deflect the rod than if the channels were not present. Spaced-apart grooves 118 extend along a majority of a length of IM rod 110 and have a thickness such that the grooves extend between flat surfaces 116A, 116B along the central section. In this manner, grooves 118 provide some flexibility of IM rod 110 in the directions parallel to the planes defined by flat surfaces 116A, 116B although the rod is stiffer in such parallel directions than the directions perpendicular to such planes.

Figure 3:
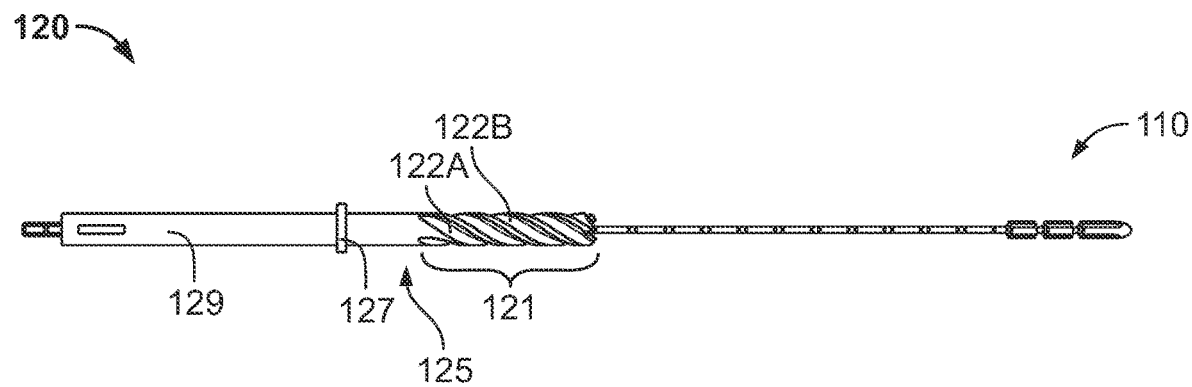
FIG. 3 is an elevation view of an assembly of the flexible IM rod shown in FIG. 2A and a reamer in accordance with an embodiment.

Referring to FIG. 3, first reamer 120 is cannulated such that the first reamer may be mounted onto and slid along rod 110. In the example shown, first reamer 120 includes cutting section 121 having a pair of helical flutes 122A, 122B on a distal portion, reamer shank 125, which as shown may have a generally smooth surface, extending from the cutting section, and connecting shaft 129 on a proximal (relative to a user) portion of the first reamer extending from reamer shank 125 for attachment to a torque driver. As shown, each of helical flutes 122A, 122B may have a right-hand helix angle such that clockwise rotation of first reamer 120 (when facing in a distal direction) may drive the reamer into bone. As further shown, cutting section 121 of first reamer 120 may be tapered such that the reamer may be self-centering during reaming as well as to reduce the amount of bone removed by the reamer while closely mimicking the shape of a stem of a revision femoral implant to be inserted into the reamed hole and providing room for adequate bone cement for fixation of the stem into bone. On an end of reamer shank 125 opposite flutes 122A, 122B, reamer shank 125 includes flange 127 extending circumferentially around a longitudinal axis of the shank. In this manner, flange 127 provides an abutment on a proximal surface of the flange to limit a depth of insertion of reamer shank 125 into bone.

Figure 4:
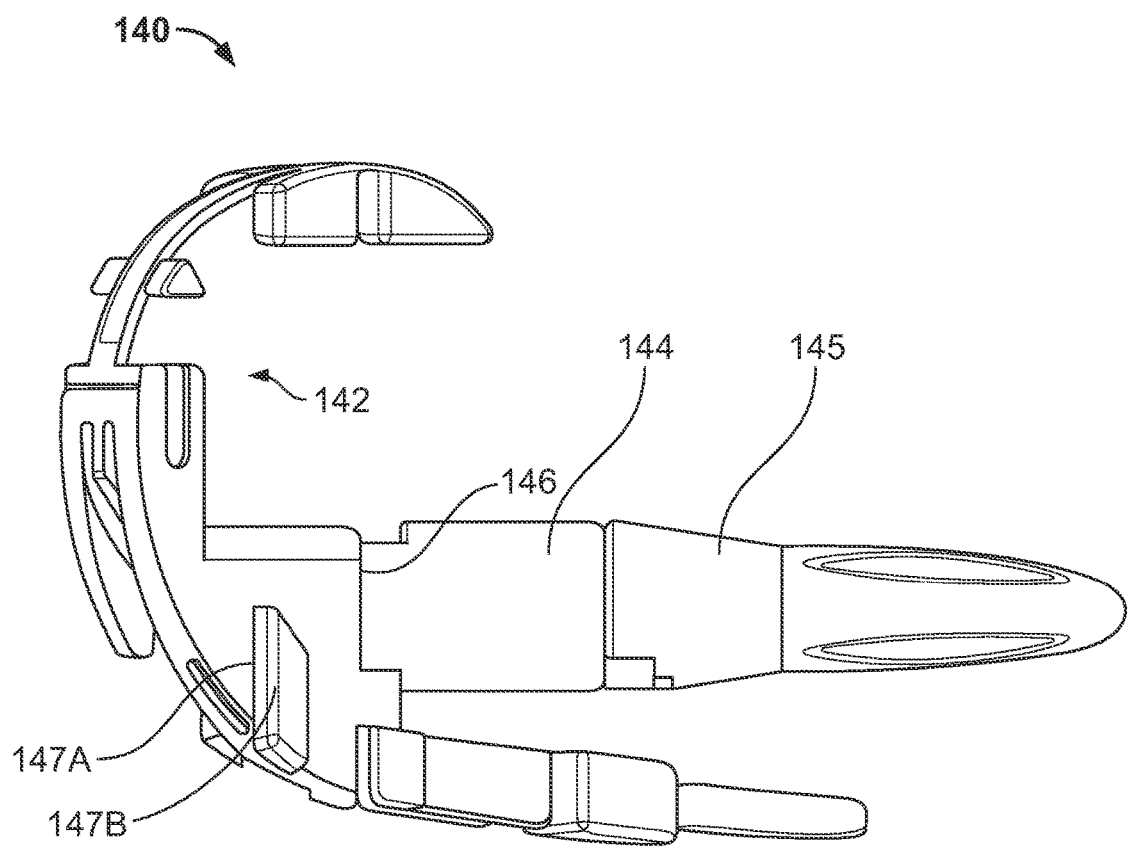
FIG. 4 is a perspective view of a trial cutting jig for placement against a distal portion of a femur as known in the art.

As shown in FIG. 4, jig 140, which in the example shown is a trial style cutting jig currently sold commercially as part of the Triathlon® TS Knee System for use in preparing a distal portion of a femur, includes cutting guide 142, adapter trial 144 that may be assembled to the cutting guide such as by threading the adapter trial to the cutting guide upon selection of an appropriately sized adapter trial, and stem trial 145 that may be assembled to the adapter trial in the form of a peg such as by threading the stem trial to the adapter trial upon selection of an appropriately configured stem trial. In this example, an outside diameter of adapter trial 144 is sized to correspond to an outside diameter of reamer shank 125 of first reamer 120 such that jig 140 may be inserted into a reamed hole in a bone prepared by the first reamer. Stem trial 145 tapers inwardly towards one end and includes channels, four equally spaced apart channels in the example shown, to ease the insertion of adapter trial 144 and stem trial 145 into the reamed hole. Cutting guide 142 includes lateral surface 146 to limit the depth of insertion of jig 140 into the reamed hole in the bone. In this example, adapter trial 144 is shown as a neutral adapter trial, although offset adapter trials, e.g., adapter trials with 2 mm, 4 mm, 6 mm, or 8 mm offsets, may be used when a femoral offset is determined to be needed as in the example of the Triathlon® TS Knee System.

Figure 5:
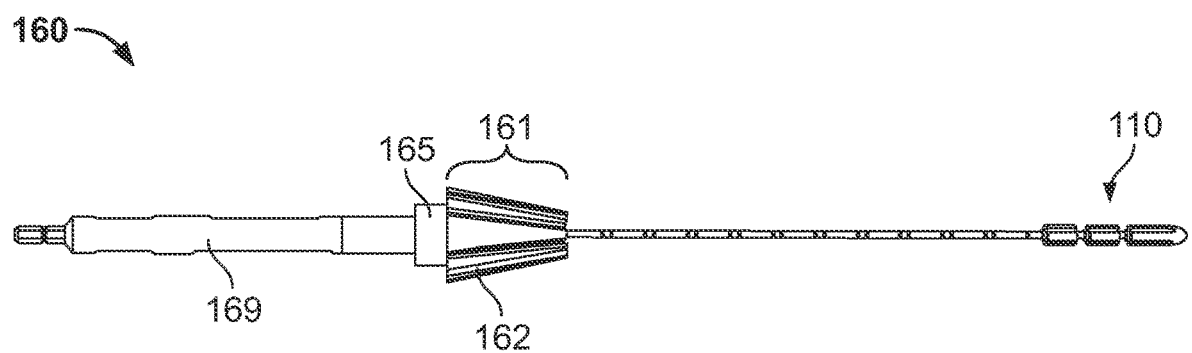
FIG. 5 is an elevation view of an assembly of a flexible IM rod shown in FIG. 2A and a symmetric cone reamer as known in the art.

Referring to FIG. 5, second reamer 160 is cannulated such that the second reamer may be mounted onto and slid along IM rod 110. In the example shown, second reamer 160 includes cutting section 161 having a plurality of straight flutes 162 on a distal portion, attachment shaft 169 on a proximal (relative to a user) portion for attachment to a torque driver, and shank 165 attaching and providing a stepped transition between the cutting section and the connecting shaft. As shown, cutting section 161 may be tapered to prepare the bone to receive a void filling prosthesis, which may be a cone augment implant, having an outer surface with dimensions approximately matching a tapered hole that may be prepared by the cutting section. As further shown, shank 165 has an outer diameter less than an outer diameter of cutting section 161 such that the shank does not contact bone during use of second reamer 160 and greater than an outer diameter of attachment shaft 169 to provide greater integrity to the second reamer at the transition from the connecting shaft to the cutting section when second reamer 160 is rotated at high speeds by the torque driver.

Figure 6:
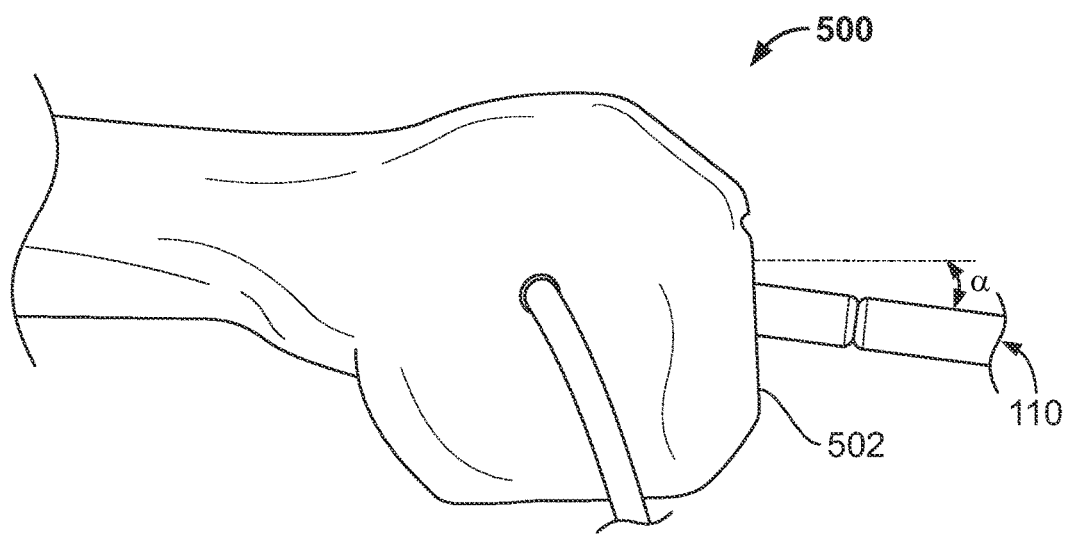
FIG. 6 is an elevation view of the flexible IM rod shown in FIG. 2A inserted into an anatomical bone model in accordance with an embodiment.

Referring now to FIG. 6, during a revision surgery, an existing stem of an implant cemented to a patient's bone is removed from the bone. In the particular example shown and as further discussed in this example, a stem of a femoral component of a knee implant system (which may be a total knee implant system including tibial and patella components as known to those skilled in the art) and inserted into and cemented to a distal portion of the patient's femur is removed from the femur. As shown in FIG. 6, IM rod 110 is then inserted into a portion of the cavity left by the removed femoral component and further inserted into a medullary canal of the patient's femur (modeled herein by anatomic bone model 500 as shown in FIG. 6), such as by an "introducer" tool as disclosed in the '541 patent. Rod 110 is so inserted such that a portion of the rod extends beyond the distal end of the femur while a majority of the rod extends within the medullary canal. As shown in FIG. 6, the portion of the rod extending beyond the distal end of the femur may extend at an angle α to a plane perpendicular to distal cut surface 502 originally cut in preparation for mounting the removed femoral component. Within bone 500, rod 110 bends along an arc and curves generally in a posterior direction.

With reference to FIGS. 2A, 2B, 3, and 6, upon insertion of IM rod 110 into bone 500, first reamer 120 is placed, i.e., mounted, onto the rod such that the rod extends through a cannula of the first reamer beyond a proximal end (relative to a user) of connecting shaft 129 of the reamer. As an example, first reamer 120 may be a 16 mm-14 mm tapered reamer for use in preparing bone 500 to receive a 12 mm×50 mm femoral knee component while conserving bone stock. During reaming with first reamer 120 placed over IM rod 110, the reamer may be forced, such as by pushing or pulling on power equipment attached to and used to drive the reamer, posteriorly. In this manner, an anterior portion of the distal portion of the femur will be preserved relative to the use of straight rigid IM rods for use in guiding such reamers. As first reamer 120 is larger than the hole left by the removed femoral component and in light of the taper of cutting section 121 of the reamer, the reamer will self-align during reaming as the reamer slides along rod 110.

Referring now to FIGS. 3, 4, and 6, in this example, after removing first reamer 120 and IM rod 110, jig 140 is inserted into the hole reamed by first reamer 120 such that a combination of adapter trial 144 and stem trial 145 extend into the prepared hole and such that lateral surface 146 of cutting guide 142 of jig 140 abuts distal cut surface 502 of rod 110 to limit the depth of insertion of the jig. In this manner, a longitudinal axis defined by adapter trial 144 and stem trial 145 of jig 140 extends at the angle α to a plane perpendicular to distal cut surface 502. Jig 140 includes cutting surfaces for guiding a cutting tool such as a reciprocating saw in making planar distal as well as anterior and posterior box cuts, e.g., cutting surfaces 147A, 147B for making a distal cut corresponding to an inner distal surface of a revision femoral knee component to be inserted into the patient's femur. Due to the angle of inclination of the combination of adapter trial 144 and stem trial 145 of reamer 120 relative to bone 500, the cuts to be made with such cutting surfaces will be offset by the angle α relative to the corresponding cuts made for preparing the bone for the original implant. Generally, such cuts may be made when jig 140 is pinned to bone 500. In the example shown, jig 140 is a 12 mm×50 mm trial style cutting jig with a neutral adapter trial, although offset adapter trials may be used when a femoral offset is determined to be needed.

Figure 7:
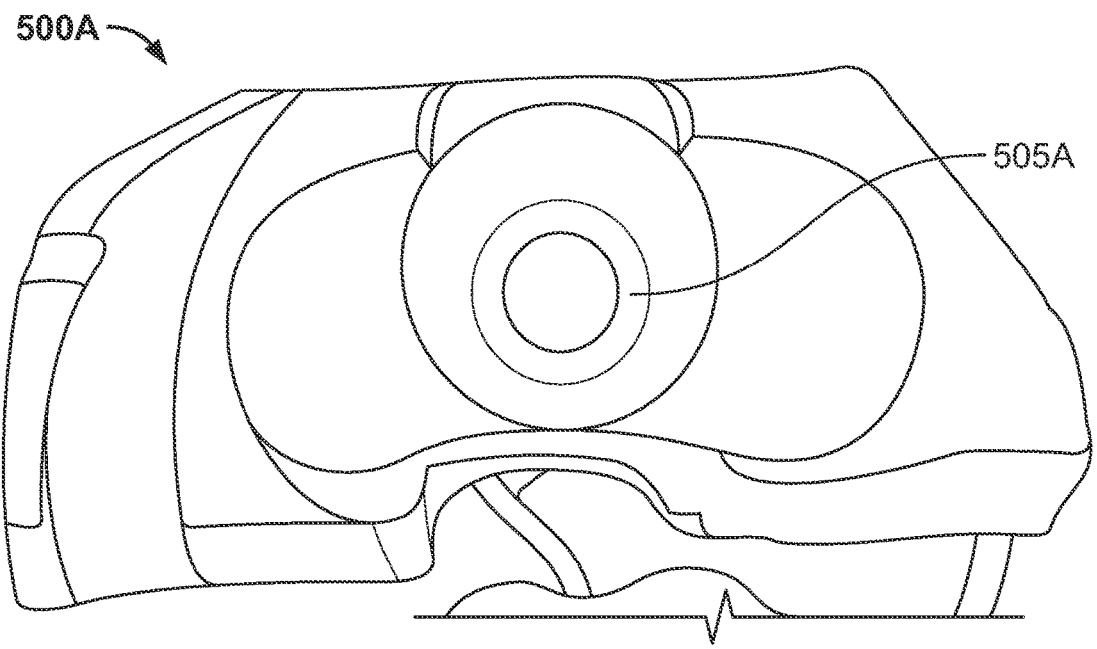
FIG. 7 is a plan view of an anatomical bone model following reaming in accordance with an embodiment.

With reference to FIGS. 4, 6 and 7, IM rod 110 may be reinserted into the prepared, i.e., formed, hole extending into the distal portion of the femur along the arc that the rod followed during the initial insertion of the rod. Upon such insertion of rod 110, second reamer 160 is placed onto the rod such that the rod extends through a cannula of the second reamer beyond a proximal end (relative to a user) of attachment shaft 169 of the reamer. In this example, second reamer 160 may be dimensioned for use in preparing bone 500 to receive a correspondingly dimensioned revision implant in which the revision implant may be in the form of a revision cone. Such a revision cone may be any one of the void filling prostheses disclosed in U.S. Pat. Nos. 9,011,444; 9,149,282; 9,526,513; 9,668,758; 10,149,763; and U.S. Patent Application Publication No. 2016/0199071 A1, the disclosures of all of which are hereby incorporated by reference in their entireties. During reaming with second reamer 160 mounted onto IM rod 110, the second reamer may be forced posteriorly in the same or similar manner as described previously herein with respect to first reamer 120, and the second reamer may be visually aligned with the tapered hole prepared by first reamer 120, as shown by reamed hole 505A of bone 500A following reaming by second reamer 160. In this manner, a greater amount of an anterior portion of the distal portion of the femur will be preserved relative to the use of straight rigid IM rods for use in guiding such reamers. A revision implant, such as a revision cone, may then be press fit into place into reamed hole 505A and subsequently a femoral knee component may be attached to the revision cone. Overall, the proper positioning of such revision cone and femoral knee component results in improved patella tracking along the condylar surfaces of the femoral knee component as well as greater stability of the knee system leading to improved femoral kinematics during flexion of the knee.

Referring now to FIGS. 8-12, an instrumentation system for preparing a bone, in particular a long bone such as a femur, to receive an implant, in particular a revision implant, generally includes intramedullary (IM) rod 110, first reamer 220, trial stem 230, distal cut jig 240, stem extender 250, multi-cut jig 270, second reamer 160, and implant 290. Each of first reamer 220, distal cut jig 240, multi-cut jig 270, and second reamer 160 are configured to be mounted on and to slide along IM rod 110. Additionally, a maximum diameter of extender shank 252 of stem extender 250 is the same or substantially the same as a maximum diameter of IM rod 110 such that each of first reamer 220, distal cut jig 240, second reamer 160, and multi-cut jig 270 are also configured to be mounted on and to slide along the extender shank although the first reamer generally would not be slid along the extender shank as the first reamer is needed to form a hole for insertion of trial stem 230, attached to the stem extender 250, into prepared bone 500.

Figure 8:
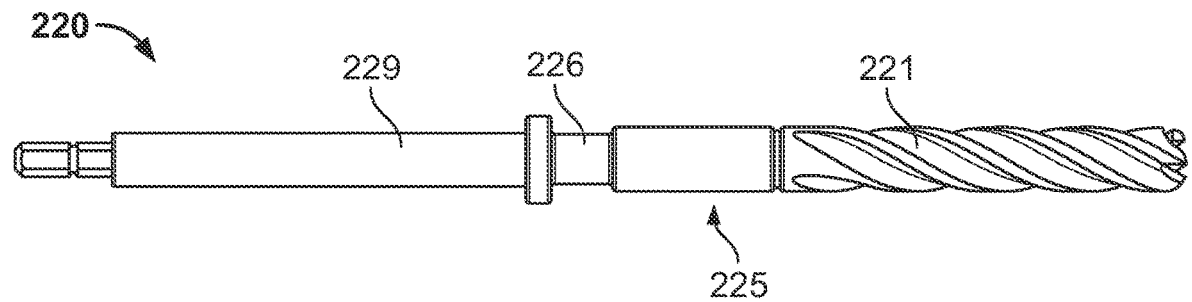
FIG. 8 is an elevation view of a reamer in accordance with an embodiment.

As shown in FIG. 8, first reamer 220 is the same or substantially the same as first reamer 120 with the notable exception that first reamer 220 includes reamer shank 225 in place of reamer shank 125 in which reamer shank 225 includes groove 226 and further includes cutting section 221 in place of cutting section 121 in which cutting section 221, as shown, may be straight rather than tapered. Groove 226 of reamer shank 225 may provide relief along the reamer shank for the removal of bone material during reaming. In some further alternative arrangements, however, a first reamer substantially in the form of first reamer 220 may not include groove 226 and may have a tapered cutting section.

Figure 9A:
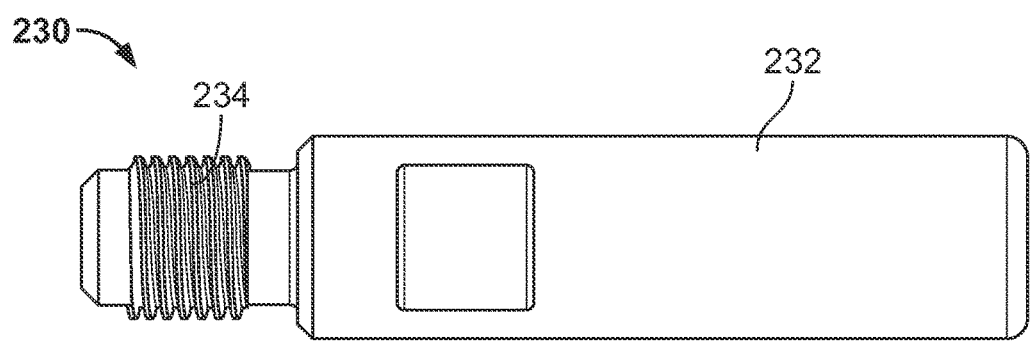
FIG. 9A is an elevation view of a trial stem in accordance with an embodiment.
Figure 9B:
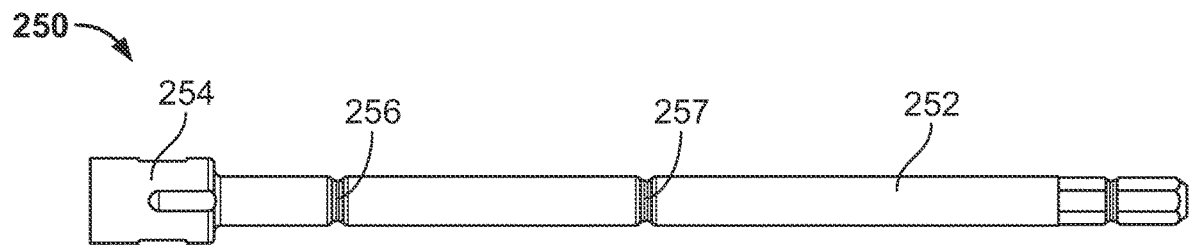
FIG. 9B is an elevation view of a stem extender in accordance with an embodiment.
Figure 9C:
FIG. 9C is an elevation view of the trial stem of FIG. 9A inserted into the stem extender of FIG. 9B.

With reference to FIGS. 9A-9C, stem extender 250 may be attached to trial stem 230 and the combination then may be inserted into a bone hole formed by first reamer 220. As shown in FIG. 9A, trial stem 230 includes stem barrel member 232, which is configured for receipt in the hole reamed by first reamer 220 to a preset depth set by the first reamer, and stem attachment portion 234 extending from the stem barrel member. Stem barrel member 232 preferably has a diameter that is substantially the same as a maximum diameter of cutting section 221 such that stem barrel member 232 forms a tight fit with the hole reamed by first reamer 220 when the stem barrel member is received in the hole. In this manner, trial stem 230 may be placed at a preset depth into the reamed hole such that a face at a proximal end (relative to a user) of stem barrel member 232 defines a limit stop for instrumentation, such as distal cut jig 240, second reamer 160, and multi-cut jig 270, placed onto stem extender 250 attached to trial stem 230.

As shown in FIG. 9B, stem extender 250 includes extender shank 252 and extender attachment portion 254 extending from the extension shank. Extender shank 252 may have a fixed diameter that is less than, preferably no more than 10% less than and more preferably no more than 5% less than, a fixed diameter of a bore through cannulated components such as second reamer 160, that may be placed over the shank. The bore through such cannulated components is preferably 5/16 inches. As in the example shown, extender shank 252 may include a first depth marking 256 and a second depth marking 257 spaced from the first depth marking. In the example shown, first depth marking 256 is in the form of a circumferential groove providing an indicium visible to the naked eye and corresponds to a depth of insertion of combined trial stem 230 and stem extender 250 for use without the insertion of a femoral cone inserted into reamed hole 505A. In this example, second depth marking 257 is also in the form of a circumferential groove providing an indicium visible to the naked eye that corresponds to a depth of insertion of combined trial stem 230 and stem extender 250 for use with the insertion of a femoral cone into reamed hole 505A. In this example, first depth marking 256 is located at 140 mm from a distal end (relative to a user) of stem barrel member 232, i.e., the distal end of the combined of trial stem 230 and stem extender 250, which upon insertion of the combined trial stem and stem extender with a cone present is aligned with the distal femoral transverse cut, i.e., the most distal cut on the distal femur. In the example, second depth marking 257 is located at 90 mm from the distal end (relative to a user) of the combined trial stem 230 and stem extender 250, which upon insertion of the combined trial stem and stem extender without a cone present is aligned with the distal femoral transverse cut.

As further shown, extender shank 252 of stem extender 250 may be solid through its core such that the shank is non-cannulated. As in the example shown, extender attachment portion 254 is a threaded female member and stem attachment portion 234 is a threaded male member configured for threaded engagement with the extender attachment portion. In some alternative arrangements, the configuration may be reversed such that the extender attachment portion may be a male member and the stem attachment portion may be a female member.

Referring again to FIG. 6, during a revision surgery, an implant such as a femoral component cemented to a patient's bone is removed from the bone, including the stem of the implant inserted into a cavity of the bone, as in the prior examples described above. As shown in FIG. 6, IM rod 110 is then inserted into a portion of the cavity left by the removed femoral component and further inserted into a medullary canal of the patient's femur (as modeled by anatomic bone model 500), such as by the introducer tool disclosed in the '541 patent, such that a portion of the rod extends beyond the distal end of the femur while a majority of the rod extends within the medullary canal. As in the prior examples above, the portion of the IM rod 110 extending beyond the distal end of the femur may extend at an angle α to a plane perpendicular to distal cut surface 502 originally cut in preparation for mounting the removed femoral component, and within the bone, rod 110 may bend along an arc and curve generally in a posterior direction.

With reference to FIGS. 2A, 2B, 6, and 8 upon insertion of IM rod 110 into bone 500, first reamer 220 is placed, i.e., mounted, onto the rod such that the rod extends through a cannula of the second reamer beyond a proximal end (relative to a user) of connecting shaft 229 of the reamer in a manner similar to the placement of first reamer 120 onto the rod as shown in FIG. 3. As an example, first reamer 220 may be a 16 mm-14 mm straight reamer for use in preparing a hole in bone 500 to receive a 12 mm×50 mm femoral knee component while conserving bone stock. During reaming with first reamer 220 placed over IM rod 110, the reamer may be forced posteriorly such that, as with first reamer 120 described previously herein, an anterior portion of the distal portion of the femur will be preserved relative to the use of straight rigid IM rods for use in guiding such reamers. In some arrangements, a user of first reamer 220 may initially use a reamer of a smaller diameter than first reamer 220 or may use a set of progressively larger reamers that are all of a smaller diameter than the first reamer in preparing the hole in bone 500 prior to using the first reamer.

Figure 10A:
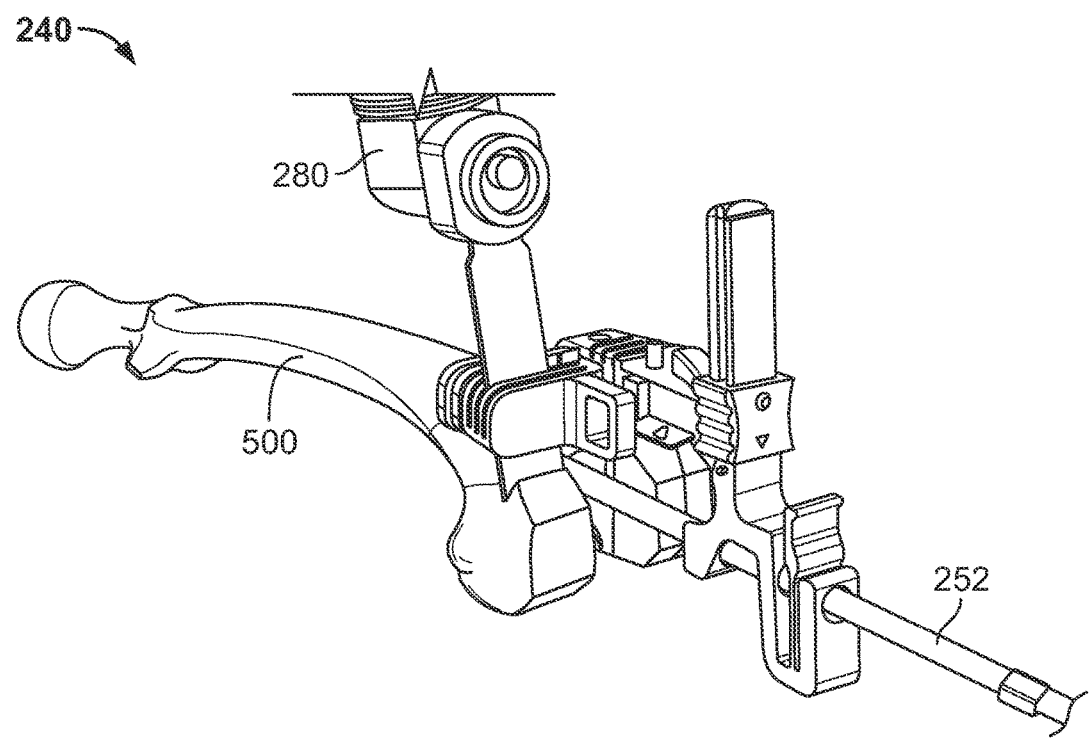
FIG. 10A is a perspective view of a bone and a distal cut jig being used to prepare a distal cut on the bone in accordance with an embodiment.

Referring now to FIG. 10A, in this example, after removing first reamer 220 and IM rod 110 from the prepared hole, stem barrel member 232 of combined trial stem 230 and stem extender 250 is inserted into the prepared hole. Distal cut jig 240 is then placed onto extender shank 252 of stem extender 250 and a cutting device, such as reciprocating saw 280 shown, is used to form a planar distal cut on bone 500 in the same manner described with respect to the Revision Distal Resection Guide in the Triathlon® Revision Knee System Surgical Protocol, 2016 ("Revision Protocol"), the disclosure of which is hereby incorporated by reference herein. Due to the angle of inclination of combined trial stem 230 and stem extender 250 relative to bone 500, the planar distal cut is offset by the angle α relative to the corresponding cut made for preparing the bone for the original femoral component.

Figure 10B:
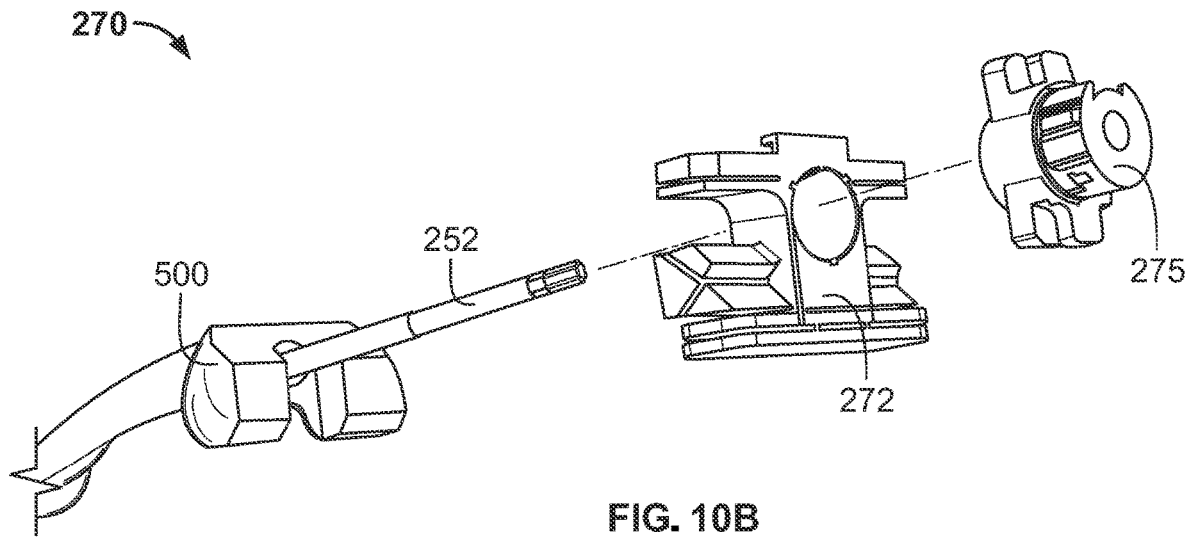
FIG. 10B is an exploded view of a multi-cut jig, a bushing, and a bone to be prepared using the multi-cut jig in accordance with an embodiment.
Figure 10C:
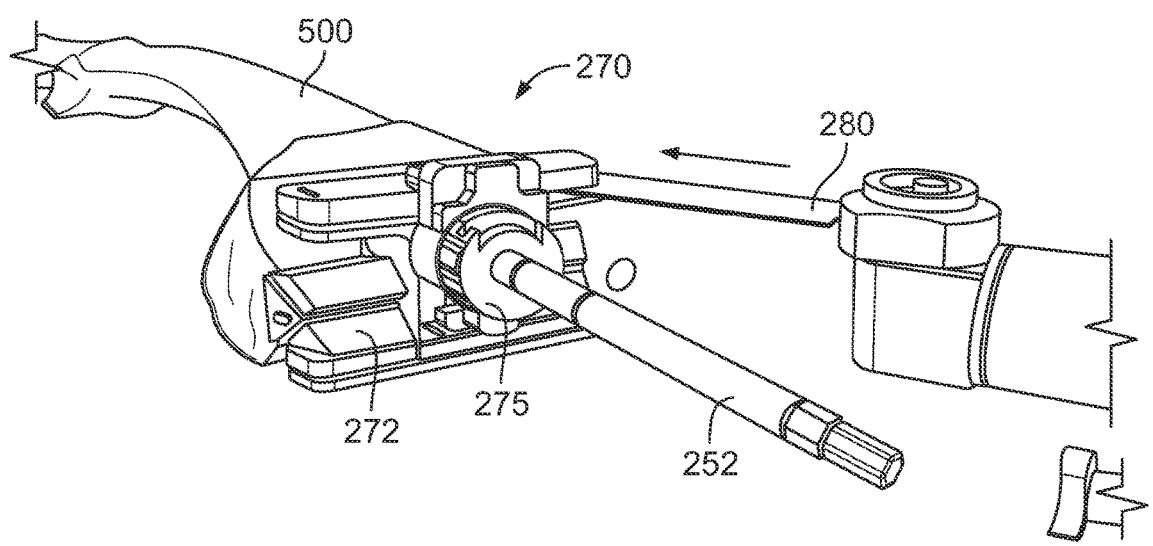
FIG. 10C is a perspective view of the bushing of FIG. 10B assembled to the multi-cut jig assembled to the bone in accordance with an embodiment.

Referring now to FIGS. 10B and 10C, after removing distal cut jig 240 from the combined trial stem 230 and stem extender 250, resection guide 272 and bushing 275 of multi-cut jig 270 may be placed, i.e., mounted, onto extender shank 252 of combined trial stem 230 and stem extender 250 still extending from bone 500 and assembled together such that the multi-cut jig is in abutment with the formed planar distal cut on bone 500 in the same manner described with respect to the All-in-One Resection Guide and Femoral Offset Bushing in the Revision Protocol. Multi-cut jig 270 includes cutting surfaces for guiding a cutting tool such as reciprocating saw 280 in making anterior and posterior box cuts and chamfers corresponding to surfaces of a revision femoral knee component to be inserted into the patient's femur. Due to the angle of inclination of the combined trial stem 230 and stem extender 250 relative to bone 500, the cuts to be made with such cutting surfaces will be offset by the angle α relative to the corresponding cuts made for preparing the bone for the original implant. Generally, such cuts may be made when multi-cut jig 270 is pinned to bone 500 as further described in the Revision Protocol.

Figure 11:
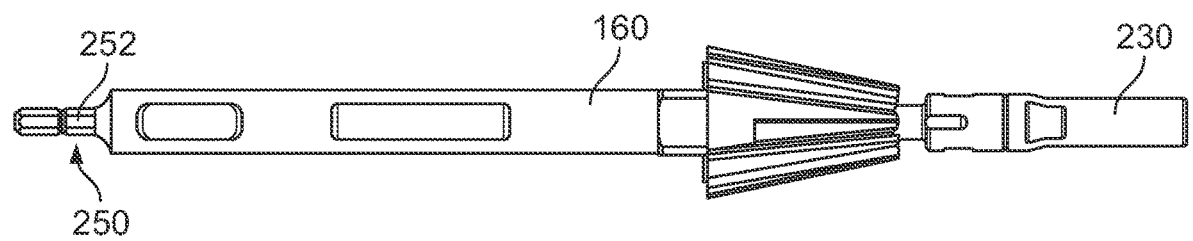
FIG. 11 is an elevation view of the symmetric cone reamer shown in FIG. 5 mounted onto combined trial stem and stem extender shown in FIG. 9B in accordance with an embodiment.

As shown by FIG. 11, after removing multi-cut jig 270 from the combined trial stem 230 and stem extender 250, second reamer 160 may be placed, i.e., mounted, onto extender shank 252 of combined trial stem 230 and stem extender 250 still extending from bone 500 such that the extender shank extends through a cannula of the second reamer beyond a proximal end (relative to a user) of attachment shaft 169 of the reamer. In this example, second reamer 160 may be dimensioned for use in preparing bone 500 to receive a correspondingly dimensioned revision implant in which the revision implant may be in the form of a revision cone, such as those discussed above. During reaming with second reamer 160 mounted onto stem extender 250, the second reamer may be forced posteriorly in the same or similar manner as described previously herein with respect to first reamer 220, and the second reamer may be visually aligned with the hole prepared by first reamer 220, as shown by reamed hole 505A of bone 500A following reaming by second reamer 160. In this manner, a greater amount of an anterior portion of the distal portion of the femur will be preserved relative to the use of straight rigid IM rods for use in guiding such reamers. A revision implant, such as a revision cone, may then be press fit into place into reamed hole 505A.

Figure 12:
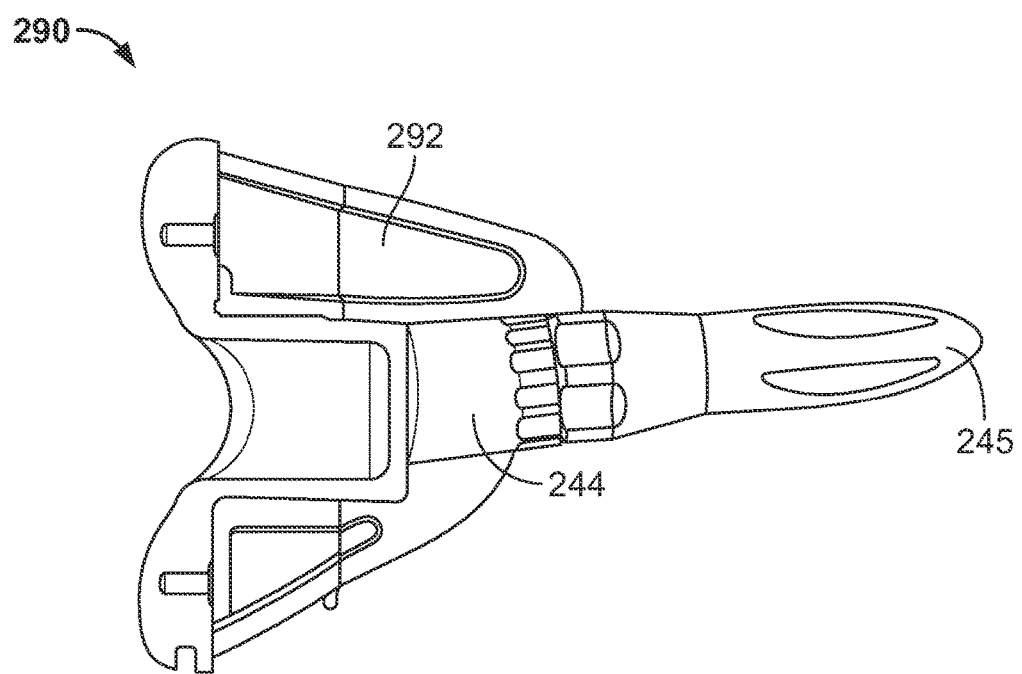
FIG. 12 is a partial cross-sectional view of an implant in accordance with an embodiment.

Subsequently, a femoral knee component, such as implant 290 in the form of a femoral knee component as shown in FIG. 12, may be attached to the revision cone. Implant 290 includes main body 292, adapter implant 244 extending from the main body, and stem implant 245 configured to be threaded to the adapter implant in which the adapter implant and the stem implant are configured for insertion into the hole prepared by first reamer 220. Overall, the proper positioning of such revision cone and implant 290 results in improved patella tracking along the condylar surfaces of the femoral knee component as well as greater stability of the knee system leading to improved femoral kinematics during flexion of the knee.

Figure 13:
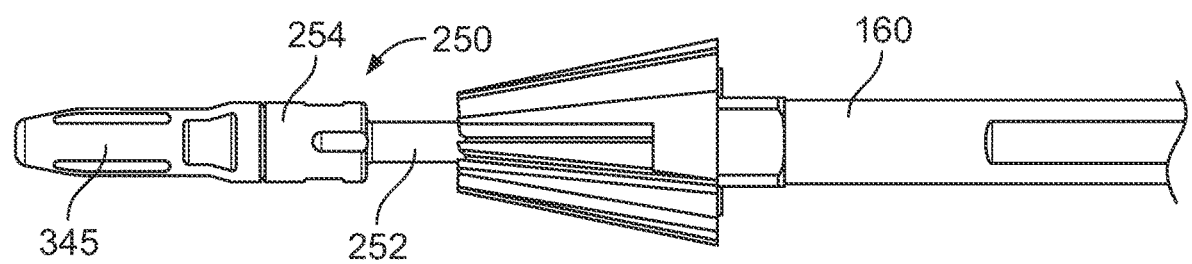
FIG. 13 is an elevational view of the symmetric cone reamer shown in FIG. 5 mounted onto a combined adapter and stem extender in accordance with an embodiment.

As shown in FIG. 13, in some alternative arrangements, stem trial 345 may be used in place of trial stem 230. Unlike trial stem 230 which has a blunt end on the distalmost end of barrel member 232 of the stem, stem trial 345 has a bullet-like shape allowing for easier insertion of a combination of stem extender 250 and stem trial 345 threaded into the stem extender.

Figure 14:
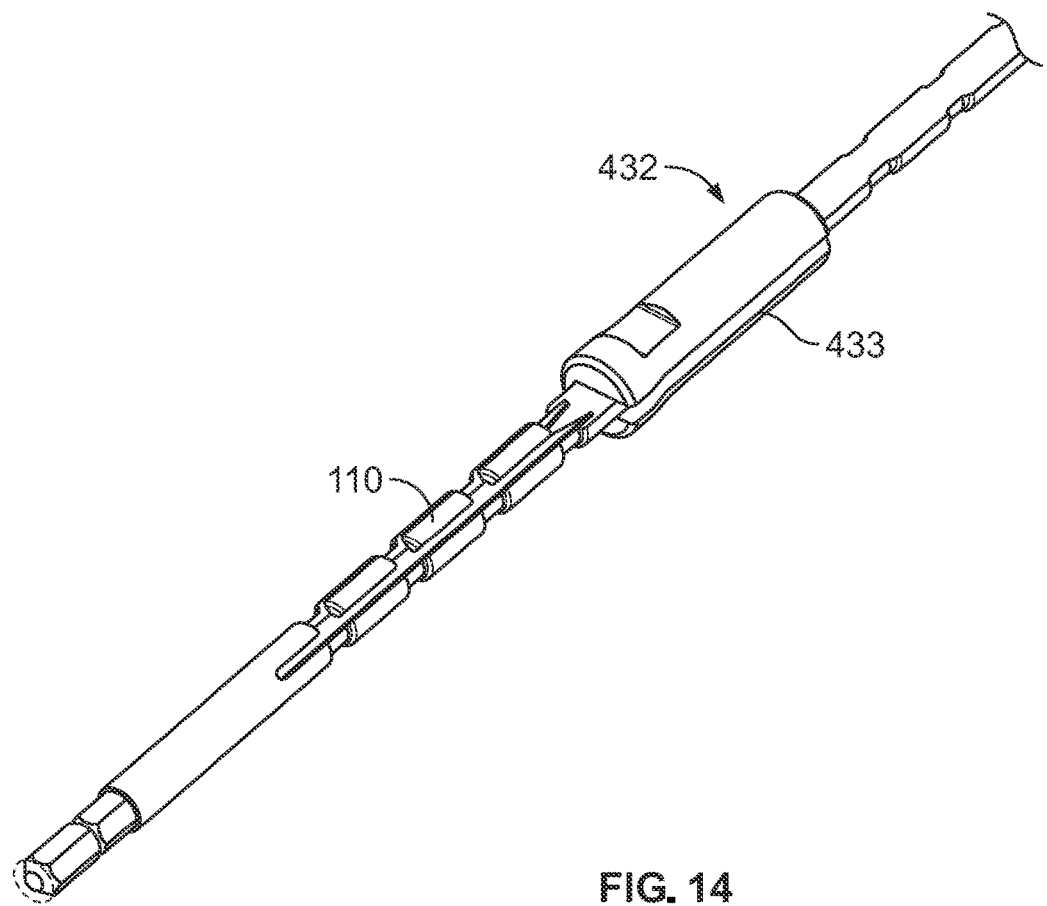
FIG. 14 is a perspective view of a barrel member placed onto the flexible IM rod shown in FIG. 2A in accordance with an embodiment.

As shown in FIG. 14, in some alternative arrangements, combined IM rod 110 and barrel member 432 may be used in place of combined trial stem 230 and stem extender 250. As shown, barrel member 432 includes slot 433 such that IM rod 110 may be received through the slot with the barrel wrapped around the slot. Like barrel member 232 of trial stem 230, the depth of barrel member 432 may be set by the depth of the hole prepared by first reamer 220. In arrangements using barrel member 432, IM rod 110 does not need to be removed from bone 500 until implant 290 is to be inserted into bone 500 as each of distal cut jig 240, second reamer 160, and multi-cut jig 270 may be mounted onto IM rod 110 and abut barrel member 432 inserted into bone 500 such that the barrel member provides a limit stop for the depth of insertion of these instruments.

In some alternative arrangements, first reamer 120, 220 may be replaced by a drill having helical flutes. In some alternative arrangements, IM rod 110 may be replaced by any one of IM rod 100, 200, 300, 400 shown in the '541 patent.

It is to be understood that the disclosure set forth herein includes all possible combinations of the particular features set forth above, whether specifically disclosed herein or not. For example, where a particular feature is disclosed in the context of a particular aspect, arrangement, configuration, or embodiment, that feature can also be used, to the extent possible, in combination with and/or in the context of other particular aspects, arrangements, configurations, and embodiments of the invention, and in the invention generally.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of performing a revision on a bone, comprising the steps of:
   placing a first cutting tool over a rod inserted into and curved within the bone such that the rod extends through a cannula of the first cutting tool, the inserted rod defining a curved longitudinal axis prior to placing the first cutting tool over the rod; and
   forming a hole in the bone with the first cutting tool placed over the curved rod.

2. The method of claim 1, further comprising the step of inserting at least a portion of a jig into the formed hole and against an end of the bone.

3. The method of claim 2, further comprising the step of removing the inserted rod from the bone prior to the jig inserting step.

4. The method of claim 2, further comprising the step of inserting a second cutting tool between a set of spaced apart cutting guide surfaces of the jig to guide the second cutting tool in cutting the bone.

5. The method of claim 4, wherein the set of cutting guide surfaces guide the second cutting tool in cutting a new planar surface of the bone defining a plane set at an angle to a plane defined by an initial planar surface of the bone existing prior to the second cutting tool inserting step.

6. The method of claim 5, wherein the initial planar surface is a distal surface, an anterior surface, or a posterior surface of the bone.

7. The method claim 2, wherein the jig includes a base and a peg extending from the base, and wherein the jig inserting step includes abutting the base against an exterior surface of the bone and inserting the peg into the formed hole.

8. The method of claim 7, wherein the exterior surface of the bone is a distal surface of the bone, and wherein the jig inserting step abuts the base against the distal surface to limit the depth the peg is inserted into the formed hole.

9. The method of claim 1, wherein the jig is a cutting jig for use in the resection of condyles of the bone.

10. The method of claim 1, wherein the first cutting tool is a drill or a reamer, wherein the hole forming step includes either drilling or reaming the hole in the bone depending on whether the first cutting tool is a drill or a reamer.

11. The method of claim 10, wherein the first cutting tool is tapered along its length.

12. The method of claim 10, further comprising the steps of:
- placing an additional cutting tool over the rod such that the rod extends through a cannula of the additional cutting tool; and
- drilling or reaming the hole with the additional cutting tool to modify the hole.

13. The method of claim 12, further comprising the step of sliding the first cutting tool off the rod to separate the first cutting tool from the rod prior to the additional cutting tool placement step.

14. The method of claim 12, wherein the first cutting tool includes a helical cutting blade and the additional cutting tool has a generally frustoconical shape and includes a plurality of straight blades tapered towards a longitudinal axis of the additional cutting tool.

15. The method of claim 1, wherein the first cutting tool placing step includes sliding the first cutting tool substantially along an arc defined by the rod that is curved within the bone.

16. The method of claim 1, wherein the bone is a long bone, further comprising the step of inserting the rod into the long bone substantially along an arc to bend the rod.

17. The method of claim 16, wherein the rod is substantially straight prior to the rod inserting step.

18. The method of claim 1, further comprising the steps of:
- inserting at least a portion of a shaft into the formed hole after removing from the rod from the bone;
- inserting a jig over the shaft against an end of the bone such that a base of the jig abuts an exterior surface of the bone; and
- inserting a second cutting tool between a set of spaced apart cutting guide surfaces of the jig to guide the second cutting tool in cutting the bone.

19. A method of performing a revision on a long bone, comprising the steps of:
- inserting a substantially straight rod into the long bone such that the rod bends;
- sliding a first cutting tool over the bent rod inserted into the long bone such that the rod extends through a cannula of the first cutting tool, the first cutting tool being a tapered drill or a tapered reamer and including a helical cutting flute;
- forming a tapered hole in the bone with the first cutting tool;
- placing a jig against an end of the bone such that a base of the jig abuts an exterior surface of the bone; and
- inserting a second cutting tool between a set of spaced apart cutting guide surfaces of the jig to guide the second cutting tool in cutting the bone, the set of spaced apart cutting guide surfaces guiding the second cutting tool in cutting a new planar surface of the bone defining a plane set at an angle to a plane defined by an initial planar surface of the bone existing prior to the second cutting tool inserting step, the initial planar surface being a distal surface, an anterior surface, or a posterior surface of the bone.

20. The method of claim 19, further comprising the steps of:
- sliding the first cutting tool off the rod to separate the first cutting tool from the rod;
- then placing an additional cutting tool over the rod such that the rod extends through a cannula of the additional cutting tool, the additional cutting tool being a reamer having a generally frustoconical shape and including a plurality of straight flutes tapered generally towards a longitudinal axis of the additional cutting tool; and
- reaming the tapered hole with the additional cutting tool to modify the tapered hole.

21. The method of claim 19, further comprising the step of:
- inserting the jig into the tapered hole such that a peg extending from the base is received in the tapered hole.

* * * * *